United States Patent [19]

Bonaccorsi et al.

[11] Patent Number: 5,103,057
[45] Date of Patent: Apr. 7, 1992

[54] ACRYLAMIDE COPOLYMERS CONTAINING (METH)ACRYLAMIDE BENZENE DICARBOXYLIC UNITS

[75] Inventors: Fabrizio Bonaccorsi, Livorno; Rosario Pappa, Monterotondo; Umberto Cova, Rome; Arnaldo Roggero; Thomas P. Lockhart, both of San Donato Milanese, all of Italy

[73] Assignees: Eniricerche S.p.A.; AGIP S.p.A., both of Milan, Italy

[21] Appl. No.: 629,408

[22] Filed: Dec. 18, 1990

[30] Foreign Application Priority Data

Dec. 21, 1989 [IT] Italy .................. 22800 A/89

[51] Int. Cl.$^5$ .................. C07C 233/05; C07C 233/53; C07C 233/55
[52] U.S. Cl. ........................ 564/207; 564/192
[58] Field of Search .............. 564/207, 192; 252/389, 252/390; 525/328.2, 329.1, 329.4, 329.5; 526/216

[56] References Cited

U.S. PATENT DOCUMENTS 3,794,563  2/1974  Barker et al. ................. 435/180
4,237,253  12/1980  Jacquet et al. ................ 526/216
4,668,747  5/1987  Codel et al. .................. 526/216

FOREIGN PATENT DOCUMENTS 57-105409  6/1982  Japan .

*Primary Examiner*—Glennon H. Hollrah
*Assistant Examiner*—Shailendra Kumar
*Attorney, Agent, or Firm*—Hedman, Gibson & Costigan

[57] ABSTRACT

New acrylamide copolymers formed by (meth)acrylamide benzene dicarboxylic monomer units in accordance with the following formula:

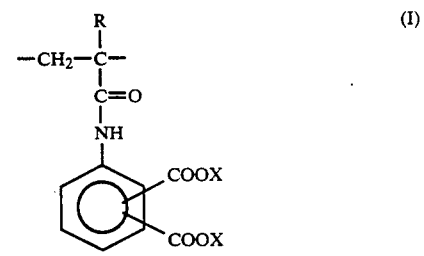

wherein R is H or $CH_3$; X is H or an alkaline metal or $NH_4$; and wherein the COOX groups may be in ortho-, meta- or para- position in relation to each other, preferably being in ortho- position to each other; and of (meth)acrylamide monomer (II) units.

8 Claims, No Drawings

ACRYLAMIDE COPOLYMERS CONTAINING (METH)ACRYLAMIDE BENZENE DICARBOXYLIC UNITS

This invention concerns new acrylamide copolymers consisting of (meta)acrylamide benzene dicarboxylic monomer units as in the following formula:

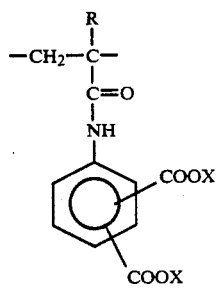

I wherein R is H or $CH_3$; X is H or alkaline metal, preferably sodium or potassium, or $NH_4$; and wherein the COOX groups may be in ortho-, meta- or para-position in relation to each other, preferably being in ortho-position to each other; and of (meth) acrylamide monomer (II) units, the molar ratio between units (I) and units (II) varying between 1:99 and 99:1.

Homopolymers and copolymers with acrylamides, containing benzene (meth) acrylamide units with the benzene ring carrying a carboxylic and an hydroxylic unit in ortho- position to each other: are known in the art.

Such polymers can form complexes with metals, for instance titanium, and as described in U.S. Pat. No. 3 794 563, these complexes may be used as solid supports for fixed enzymes. In the Japanese Patent application JP57-105409 is described the use in adhesive compounds for dental purposes of methacrylamide (iso)phthalic acid homo-polymer or of one of its copolymers with methyl methacrylate. The present invention has now found new acrylamide or methacrylamide copolymers, containing formula (I) (meth)acrylamide benzene dicarboxylic units, soluble in water and with useful applications in various fields. They may for instance be used advantageously in water treatment, to eliminate and/or recover metals or to inhibit the formation of incrustations due to deposits of insoluble salts, particularly calcium salts.

For that purpose the copolymers are used preferably with a molar ratio between formula (I) monomer units and formula (II) monomer units which varies between 70:30 and 99:1.

Copolymers in this invention may also be used with flocculants to precipitate solids suspended in water. In this case they preferably used with a molar ratio of (I):(II) between 1:99 and 30:70.

Copolymers in this invention are also water-soluble in very high concentrations and have a weight average molecular weight which goes from 1000 to 20,000,000 and preferably from 1,000,000 to 10,000,000.

They can be prepared by way of the copolymerization of monomers complying with the following formula:

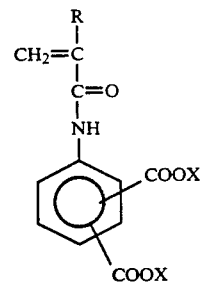

III wherein R is H or $CH_3$; X is H or alkaline metal or $NH_4$; and wherein the COOX groups may be in ortho-, meta- or para- position in relation to each other, preferably in ortho- position to each other; with (meth)acrylamide using the radical polymerization process according to known technique. Polymerization may generally be effected by operating in solution, emulsion or suspension, and is preferably achieved in solution.

Normal practice features an aqueous solution, with a pH going from 3 to 11 approximately, using radical initiators, for instance peroxides, persulphates or nitrogen compounds.

The copolymers in which X is alkaline metal or $NH_4$, may be obtained by polymerizing the relevant formula II monomers in which X is an alkaline metal or $NH_4$, or by polymerizing the monomer in the acid form (X=H) and adding to the final polymer solution the inorganic suitable base to obtain the required salt, for instance NaOH, KOH or $NH_4OH$.

In the same manner the copolymers in which X=H can be obtained by polymerizing the relevant formula II monomer in which X=H or by polymerizing the monomer in salt form (X=alkaline metal, $NH_4$) then acidifying the final polymer solution, for instance by adding hydrochloric acid or sulphuric acid.

The copolymerization reaction temperature may generally vary between ambient temperature (15°-25° C.) and 90° C. approximately and conversion of the monomers is practically complete within a period going from 30 minutes to 24 hours depending on the temperature used, the usual procedure generally featuring a temperature of 50°-70° C. for a period of 1-2 hours.

The molar ratio of the monomers thus introduced is also maintained unchanged in the final copolymer. Formula (III) (meth)acrylamide benzene dicarboxylic monomers used in the production of copolymers according to the present invention may be obtained quite simply according to known organic chemistry methodology. As an example, preparation may start with commercially available relevant nitro benzene dicarboxylic compounds, by reducing the nitro group to an amino group, for instance using the hydrogenation process on platinum oxide described in the Journal of Organic Chemistry 25, 1882 (1960), followed by condensation of the amino benzene dicarboxylic compound with (meth-)acryloyl chloride. The following examples are given for illustration purposes only and must not be considered as in any way restrictive of the scope of the invention.

EXAMPLE 1

Preparation of 3-acrylamide-1,2-benzene dicarboxylic acid

1) Reduction of 3-nitro-1,2-benzene dicarboxylic acid to 3-amino-1,2-benzene dicarboxylic acid. 21.1 g (0.1 moles) of 3-nitro-1,2-benzene dicarboxylic acid dissolved in 75 ml of water containing 8.2 g of NaOH, are placed in a 500 ml glass autoclave. The pH of the mixture is then adjusted to 8-9 by the addition of dilute acetic acid.

One gram of $PtO_2$ is then added pressurised under $H_2$ at 4 atm, after flushing 4 times with nitrogen.

The autoclave temperature is raised to 50° C. and the mixture is left to react for 24 hours. On completion the platinum oxide is then removed by filtration and 50 ml of conc. HCL are added to the filtrate. An addition of 200 ml of acetone is then made to the resultant opalescent solution to promote precipitation of the inorganic salts, which are then filtered off. The filtrate is finally concentrated until an opalescent solution is obtained, from which after cooling at 4° C., the reaction product is precipitated in the form of hydrochloride.

After filtering and drying under vacuum, 19.5 g of 3-amino-1,2-benzene dicarboxylic acid hydrochloride are obtained, representing a 90% yield.

The product structure is confirmed by IR and $^1H$-NMR spectroscope analysis.

2) Condensation with acryloyl chloride 10 g (46 mmoles) of 3-amino-1,2-benzene dicarboxylic acid hydrochloride are dissolved in 150 ml of 2N NaOH, and to the solution cooled to 0° C., a slow addition of 11 g (122 mmoles) of acryloyl chloride is then made. Having completed the addition, the mixture is stirred for two hours at ambient temperature, then extracted with ethyl acetate to eliminate non-reacted acryloyl chloride.

The aqueous phase is then acidified to pH 4 and the reaction product is recovered by precipitation at 0° C. After filtering, then washing the filter with THF and drying in a vacuum oven, 10 g of 3-acrylamide-1,2 benzene dicarboxylic acid are obtained, with a 92% yield.

The product structure is confirmed by IR and $^1H$-NMR spectroscope analysis.

EXAMPLE 2

20 g (0,282 moles) of acrylamide, 2.23g (0.0087 moles) of 3-acrylamide-1,2-benzene dicarboxylic acid and 220 ml of de-ionised water are placed in a 500 ml reactor with mechanical stirrer and condenser, then the pH is adjusted to pH 9 with an addition of 2M soda.

The mixture is left for 2 hours under nitrogen flow to remove any air contained therein, then heated to 60° C. and a solution of 85,5 mg (0.316 mmoles) of $K_2S_2O_8$ in 5 ml of de-ionised water is added quickly. The reaction is allowed to continue for 90 minutes, maintaining the temperature at 60° C.

On completion, the mixture thus obtained is cooled to ambient temperature and the polymer is recovered and refined by precipitating twice in succession with methanol at pH 10.

After drying under low pressure 23.4 g of copolymer are obtained, in the form of sodium salt (according to formula I:X=Na), equal to a practically complete conversion of the monomers.

The molar ratio between 3-acrylamide-1,2-benzene dicarboxylic and acrylamide units is 3:97.

The copolymer properties are as follows:
Weight average molecular weight: 3,700,000 (g/mole); (determined by GPC).

Intrinsic viscosity (determined in aqueous solution of 2M NaCl at 25° C.): 950 cm$^3$/g.

EXAMPLE 3

The procedure is as in example 2, with the exception that the addition of the two monomers is made with a molar ratio of 5:95 of 3-acrylamide-1,2 benzene dicarboxylic acid:acrylamide.

The conversion rate is 95% and the ratio between monomer units of the copolymer, assessed by $^{13}C$-NMR spectroscopic analysis, is practically equal to the initial rate (4.9:95.1).

The copolymer properties are as follows:
Weight average molecular weight: 8,200,000 g/mole.
Intrinsic viscosity: 1585 cm$^3$/g.

EXAMPLE 5

The procedure is as in example 2, with the exception that the 3-acrylamide-1,2 benzene dicarboxylic acid is replaced by 4-acrylamide-1,2 benzene dicarboxylic acid with a molar ratio of 5:95 to the acrylamide.

The copolymer properties are as follows:
The conversion rate is 97% and the ratio between monomer units is practically equal to the initial rate (4.7:95.3).

The properties of the copolymer thus obtained are as follows:
Weight average molecular weight: 4,400,000 g/mole.
Intrinsic viscosity: 1050 cm$^3$/g.

EXAMPLE 6

The procedure is as in example 5, with the exception that polymerization takes place with a pH 4 and the copolymer is isolated in the acid form (according to I:X=H).

The ratio between monomer units in the copolymer is 4.5:95.5.

The properties of the copolymer thus obtained are as follows:
Weight average molecular weight: 3,915,000 g/mole.
Intrinsic viscosity: 890 cm$^3$/g.

We claim:

1. An acrylamide copolymer formed from (I) monomer units of the following general formula:

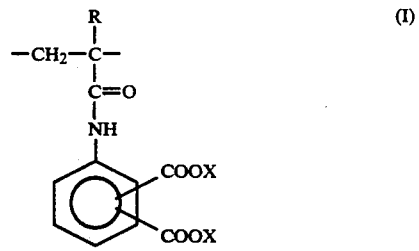

wherein R is H or $CH_3$; X is H or an alkaline metal or $NH_4$; and wherein the COOX groups may be in ortho-, meta- or para-position in relation to each other; and from (II) acrylamide or (meth)acrylamide units, the molar ratio between (I) and units (II) varying between 1:99 and 99:1.

2. A copolymer according to claim 1, wherein the alkaline metal is sodium or potassium.

3. A copolymer according to claim 1, wherein the COOX groups are in ortho- position in relation to each other.

4. A copolymer according to claim 3, wherein R is H.

5. A copolymer according to claim 1, having a weight average molecular weight ranging from 1000 to 20,000,000.

6. A copolymer according to claim 2, having a weight average molecular weight ranging from 1,000,000 to 10,000,000.

7. A copolymer according to claim 1, wherein the molecular ratio between units (I) and units (II) varies between 70:30 and 99:1.

8. A copolymer according to claim 1, wherein the molar ratio between units (I) and units (II) varies between 1:99 and 30:70.

* * * * *